United States Patent [19]

Schreiber

[11] 4,310,437

[45] Jan. 12, 1982

[54] FOAM BREAKER FOR GAS/LIQUID REACTORS

[75] Inventor: Anselm Schreiber, Essen, Fed. Rep. of Germany

[73] Assignee: Bergwerksverband GmbH, Essen, Fed. Rep. of Germany

[21] Appl. No.: 190,829

[22] Filed: Sep. 25, 1980

[30] Foreign Application Priority Data

Sep. 25, 1979 [DE] Fed. Rep. of Germany ....... 2938668

[51] Int. Cl.³ ............................................ B01D 19/02
[52] U.S. Cl. ................... 252/361; 209/169;
 210/221.2; 252/359 R; 252/359 C; 261/91;
 261/93; 366/104; 366/295; 435/315
[58] Field of Search .............. 252/359 R, 359 C, 361;
 435/313-315; 366/104, 295; 261/91, 93, DIG.
 26; 210/221 M, 221 P; 209/169, 170

[56] References Cited

U.S. PATENT DOCUMENTS

| 2,791,404 | 5/1957 | Kelly, Jr. et al. | 261/93 X |
| 3,017,951 | 1/1962 | Wiley | 261/93 X |
| 3,250,519 | 5/1966 | Herfeld | 261/93 |
| 3,491,880 | 1/1970 | Reck | 261/93 X |
| 3,625,834 | 12/1971 | Muller | 261/93 X |
| 3,704,009 | 11/1972 | Kalbskopf | 261/91 |
| 3,704,868 | 12/1972 | Weis | 261/91 |
| 3,911,065 | 10/1975 | Martin et al. | 261/91 |

FOREIGN PATENT DOCUMENTS 2518082 10/1978 Fed. Rep. of Germany .
2719112 11/1978 Fed. Rep. of Germany .

OTHER PUBLICATIONS

Rehm, Hans-Jurgen; *Einfuhrung in die Industrielle Mikrobiologie;* Springer-Verlag Berlin (1971), pp. 110, 111.

Primary Examiner—Richard L. Chiesa
Attorney, Agent, or Firm—Michael J. Striker

[57] ABSTRACT

A foam breaker for a fermentation reactor has one or more curved rods, preferably hollow rods with open ends (tubes), and an arrangement for so mounting these on the rotor of the reactor that they rotate with the rotor. The rods or the tubes have leading ends or inlets respectively which scoop up liquid of the liquid phase contained in the reactor, and opposite closed ends or outlets respectively at or through which this liquid is slung away or expelled in form of jets which pass through and destroy a layer of foam that forms above the liquid phase in the reactor.

13 Claims, 5 Drawing Figures

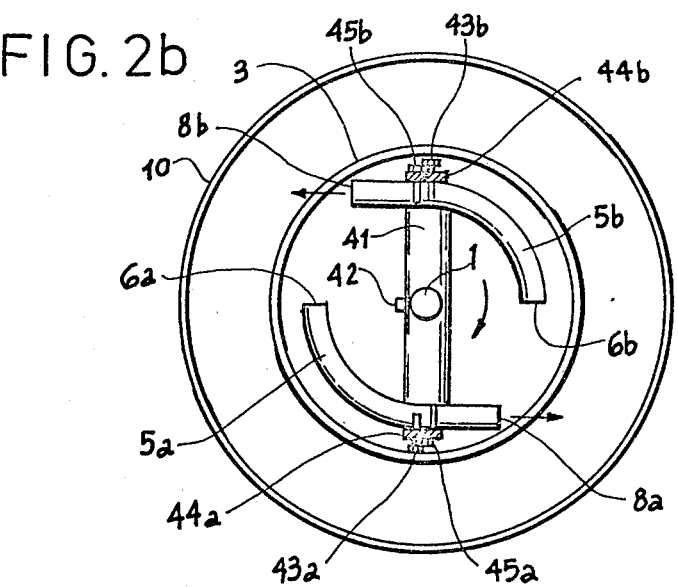
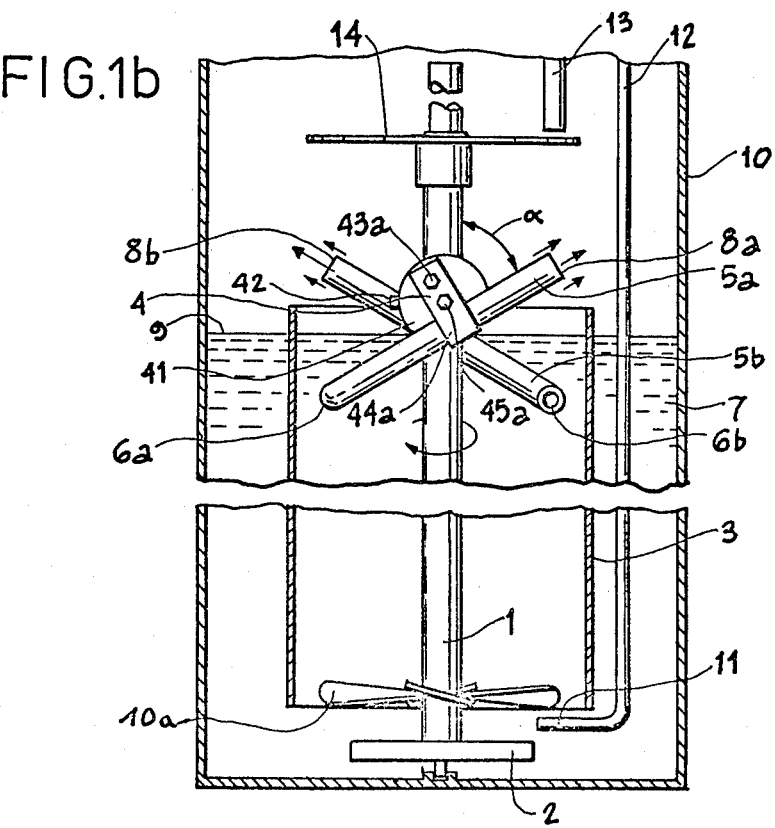

4,310,437

FOAM BREAKER FOR GAS/LIQUID REACTORS

BACKGROUND OF THE INVENTION

The present invention relates to foam breakers, and in particular to foam breakers for gas/liquid reactors (fermentors) and to reactors having such foam breakers.

Gas/liquid reactors are used, inter alia, in connection with the aerobic fermentation growth of micro-organisms. Among the most important tasks in this type of application are the need to create the largest possible interface between the gas phase and the bio-suspension liquid phase, the periodic renewal of this interface to eliminate diffusion blockages, and the uniform distribution of the micro-organism in the bio-suspension (nutrient) in order to avoid local enrichment and separation.

Ideally, the gas phase and the liquid nutrient phase should be absolutely uniformly mixed, i.e., should be completely uniformly distributed throughout. In most fermentation reactors this ideal condition cannot be attained. What happens instead is the formation of a liquid phase which is well mixed with the gaseous phase (usually aerated) and above which a layer of poorly mixed foam is formed. The formation of foam may be so strong that only 30-40% of the reactor volume can be filled with liquid, the rest being taken up by the foam. This foam formation is undesirable, because micro-organisms tend to conglomerate in the poorly mixed foam layer, with the result that local separations take place. Furthermore, the removal of waste gas (e.g., $CO_2$) which develops during the fermentation, is made more difficult by the presence of the foam. And finally, a large proportion of the bio-suspension may be lost due to the formation and overflowing of the foam, unless special steps are taken to prevent this.

The problems outlined above have been recognized in the art for some time and the solution that has been proposed is the mechanical foam breaker, sometimes called a foam separator. However, the prior-art foam breakers are all fairly complicated from a structural viewpoint and are therefore expensive.

According to one proposal, made in German Pat. No. 2,518,082, conical members are mounted in the reactor head in front of the outlet opening for the waste gas; these are rotated at high speed, causing the surrounding foam to be flung off the conical members and the foam layer thereby to be destroyed, so that the waste gas can escape through its outlet opening. The mixing of the gaseous and liquid phases is accomplished or enhanced in fermentors of the type in question by means of paddles or similar instrumentalities mounted on a rotating shaft. For the foam breaker to operate effectively, the conical members must rotate at a much higher speed than this shaft, which means that the shaft and the foam breaker each require a separate drive. This raises the overall cost and energy requirements and, of course, increases the chances of possible malfunction. Particularly in the case of smaller reactors up to, say, about 20 liter volume this can be bothersome.

According to another proposal (Rehm, Einführung in die industrielle Mikrobiologie, Springer-Verlag 1971, page 111) the foam layer is drawn off from the reactor and fed into an external foam breaker where the foam is separated into its liquid and gaseous constituents. The liquid component is continuously recirculated into the reactor. In this proposal the time between the formation and subsequent destruction of each foam bubble is relatively long, which means that the dwell time of individual parts of the bio-suspension in the poorly mixed foam layer is correspondingly long, so that local separations occur.

Still another proposal (German Published Application DE-OS No. 2,719,112) combines the earlier-mentioned conical rotary members with a tube system which operates as a gas exchanger. Again, the proposal works, but it is structurally relatively complicated and therefore only of limited applicability.

SUMMARY OF THE INVENTION

It is an object of the invention to overcome drawbacks of the prior art.

A more particular object is to provide an improved but technically simple foam breaker.

Still another object is to provide a foam breaker which does not require or permit the foam layer to move out of the reactor together with the waste (spent) gas.

A concomitant object is to provide a foam breaker of the type under discussion which, in operation, favors the development of an equilibrium between the rate of foam formation and the rate of foam destruction, so that the residence time of each individual foam bubble (i.e., the time from its generation to its destruction) is kept to a minimum.

These objects, and still others which will become apparent hereinafter, are met by providing a rotor which is to rotate in the foam-forming area of a fermentation reactor and which carries one or more (usually two or more) curved rods, preferably tubelike hollow rods with open ends (tubes). If two or more rods or tubes are used, they are mounted on the rotor in radially symmetrical relationship.

According to the invention the arrangement is such that when the rotor is rotating, the inlet opening or openings of the tube wall, in dependence upon the angle included between the tubes and the longitudinal axis of rotation of the rotor, be immersed in the liquid contents of the reactor. This assures that when the rotor comes up to operating speed, the liquid will forcibly enter the tubes and will then subsequently be ejected from their outlet openings as a liquid stream that penetrates the foam layer and splatters against the reactor wall. But liquid is also scooped up by the outer surface of the end portion of the tube or rod which is immersed in the liquid and led along the surface of the tube or rod during the rotating movement to be slung away from the other end of the tube or rod to penetrate the foam layer and splatter against the reactor wall. Advantageously, the rods or tubes are curved in the direction of rotation of the rotor—preferably the ends immersed in the liquid are directed on a concentric line in relation to the axis of the rotor.

According to another aspect of the invention the rods or tubes may be mounted on the rotor via a carrier rod having a mounting screw and mounting brackets having mounting screws and spacer screws. This permits adjustments to be made in respect of the angle of inclination of the rods or tubes relative to the rotor, as well as the distance of the rods or tube inlets from the rotor.

The novel features which are considered as characteristic for the invention are set forth in particular in the appended claims. The invention itself, however, both as to its construction and its method of operating, together with additional objects and advantages thereof, will be best understood from the following description of specific embodiments when read in connection with the accompanying drawing.

BRIEF DESCRIPTION OF THE DRAWING

FIGS. 1a and 1b are fragmentary, partly sectioned side views of a fermentation reactor including foam breakers according to the invention;

FIGS. 2a and 2b are top plan views of FIGS. 1a and 1b respectively; and

DESCRIPTION OF THE PREFERRED EMBODIMENTS

Figure 2A:
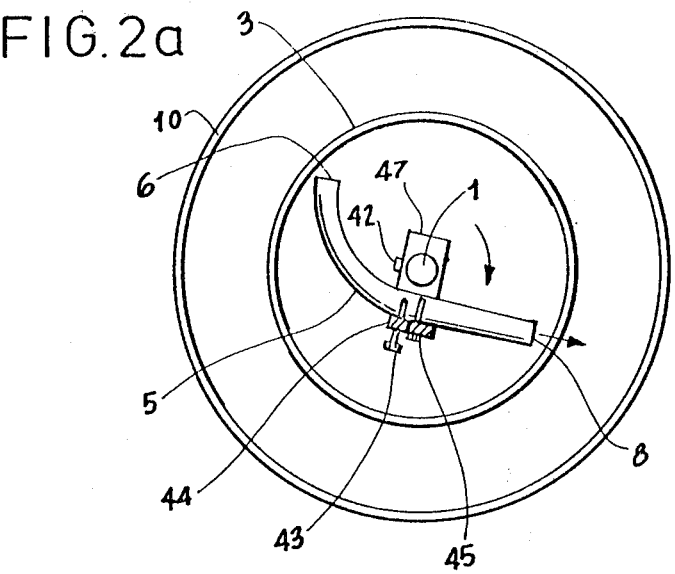
Figure 1A:
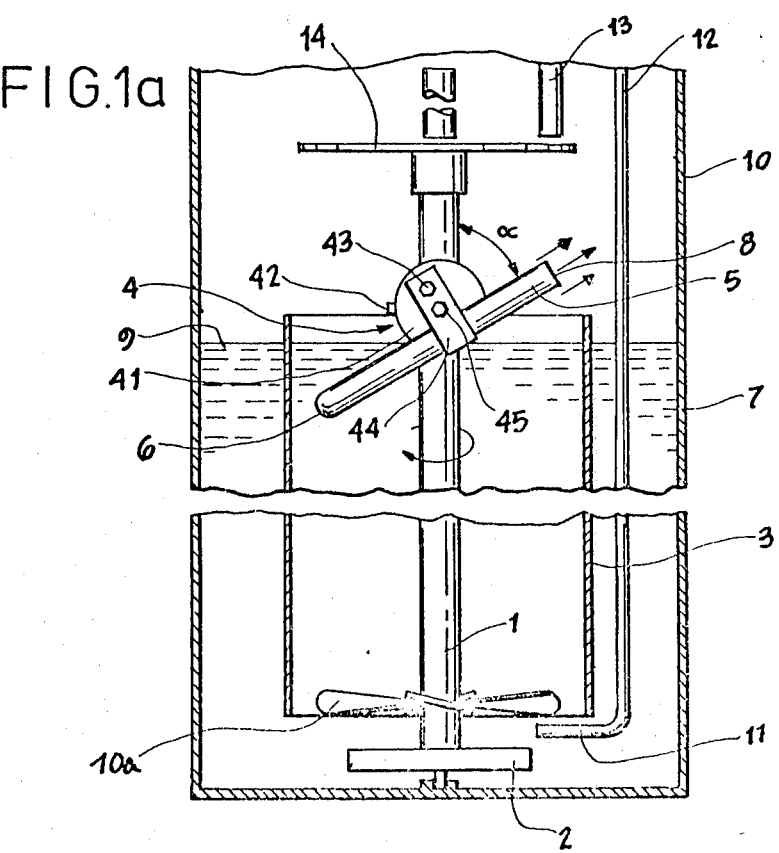

The drawing shows in FIGS. 1a, 1b and 2a, and 2b an upright vessel 10 of a fermentation reactor. The vessel is filled with liquid nutrient 7 to the level 9 and in operation of the reactor a layer of foam develops in the area extending upwardly from the level 9.

Mounted in the vessel 10 is an upright rotatable shaft (rotor) 1 which carries at its lower end a magnet 2. The shaft also carries blades or paddles 10a which agitate and circulate the liquid nutrient 7; it is surrounded with spacing by a tubular fluid guide 3. All this is known.

In accordance with the invention the rotor 1 is provided, at or near the level of the upper edge of the baffle 3, with an adjustable mount 4 for the rod 5 (FIGS. 1a and 2a) or the tubes 5a and 5b (FIGS. 1b and 2b) of the inventive foam breaker. The mount 4 includes a solid bar 41 of e.g., rust-free steel which is elongated transverse to the axis of rotation of shaft 1 and provided with a bore through which the shaft extends. A mounting screw 42 permits the bar 41 to be secured to the shaft 1 at whatever level is desired within the reactor vessel 10. A pair of mounting brackets 44a and 44b is provided, each having a recess for one of the rod 5 or the tubes 5a, 5b. Screws 45a, and 45b are provided which allow the rod 5 or the tubes 5a, 5b to be arrested in any desired position relative to the bar 41 and shaft 1. Spacer screws 43a and 43b are installed as shown and serve to enhance the mechanical stability of the brackets 44a, 44b.

The rod 5 or the tubes 5a, 5b are curved in the direction of rotation of shaft 1 (see the arrow in FIGS. 2a and 2b) and their leading inlet ends 6 or 6a and 6b are immersed in the liquid nutrient 7 (FIG. 1). The opposite ends of the rod or the tubes are straight and provided with respective closed end 8 or outlet openings 8a, 8b which are located above the liquid level 9. The inclination angle $\alpha$ between the rod 5 or the tubes 5a, 5b and the rotor 1 is 60° in the illustrated embodiment.

Figure 3:
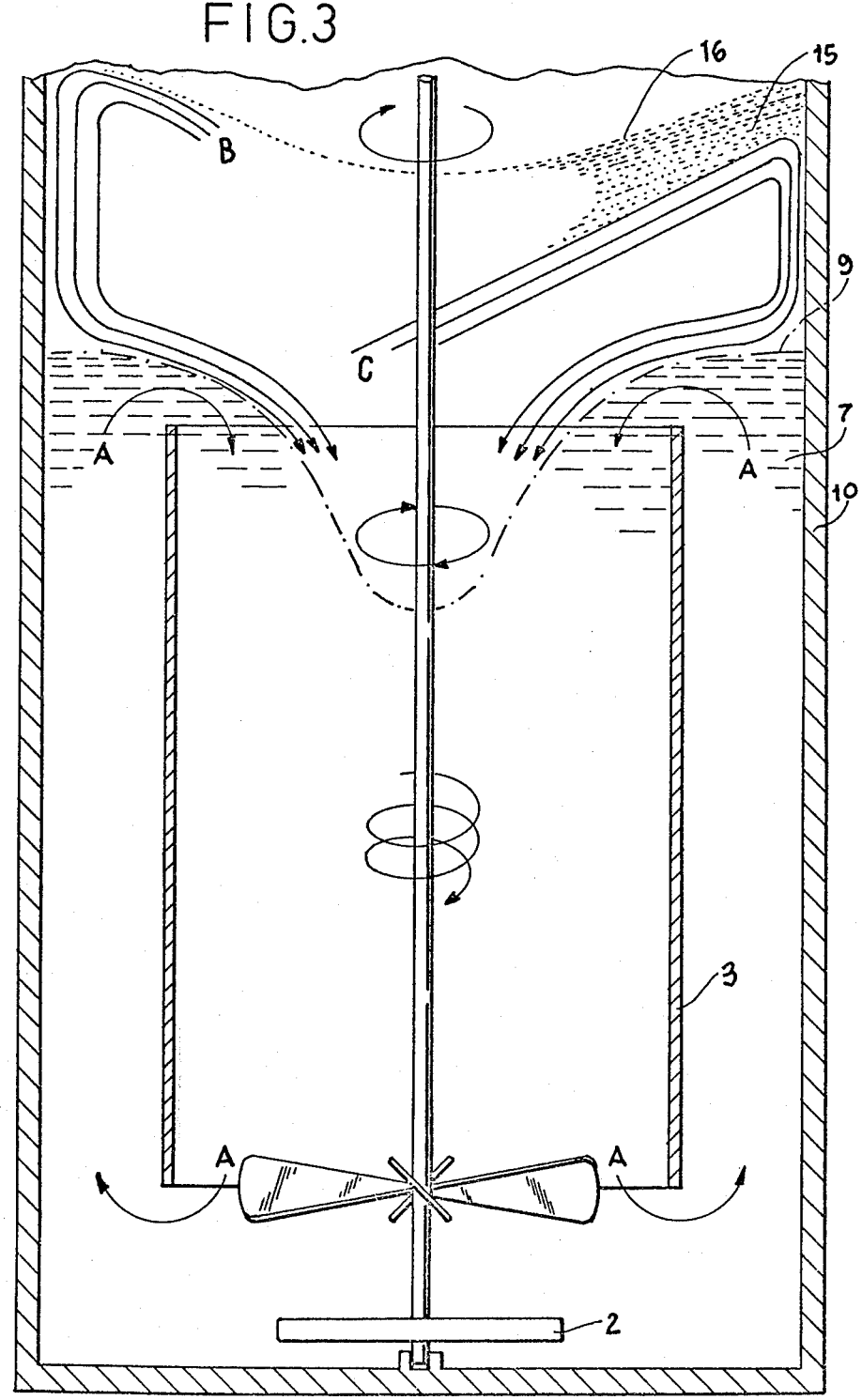
FIG. 3 is a view analogous to FIGS. 1a and b, but with the foam breaker omitted and its operating effects being schematically illustrated instead.

The shaft 1 is rotated by entrainment of its magnet 2 via an element of a drive located outside and below the vessel 10; this is known per se. As the shaft rotates, the rod 5 or the tubes 5a, 5b rotate with it and liquid 7 is forced against the leading end 6 or into the inlet openings 6a, 6b. This liquid is slung away from the closed end 8 or issues from the outlet openings 8a, 8b in form of streams respectively which penetrate the foam and splatter against the wall of vessel 10 above the foam layer 15 (FIG. 3). In addition, liquid is flung off by the immersed end portion of the rod 5 or the tubes 5a, 5b and passes through the foam layer 15 to impinge against the wall of vessel 10. A pipe 12 has nozzles 11 through which the gaseous phase (air) is admitted; spent (waste) gas leaves the vessel 10 via pipe 13 which is protected against splashing liquid by a disk 14 mounted on shaft 1 (FIG. 1).

When the shaft and foam breaker rotate at operating speed the liquid 7 circulates in the baffle 3 in downward direction and then passes upward through the space between baffle 3 and the wall of vessel 10 (arrows A in FIG. 3). In the absence of the inventive foam breaker the foam layer 15 which forms above the level 9, would be kept moving only at its interface with the level 9. Due to the streams of liquid (arrows B,C) issuing from the foam breaker, however, the entire foam layer 15 is constantly being agitated right up to its upper limit 16. The liquid streams (those designated with arrows B issue from tubes 5a, 5b and those designated with arrows C result from liquid being flung off the immersed portions of the rod 5 or the tubes 5a, 5b) constantly agitate and destroy the foam, preferably at a rate equal to the creation of new foam.

The movement of the immersed portions of the rod 5 or the tubes 5a, 5b through the liquid 7 results, of course, in the creation of additional turbulence which would be expected to contribute to the formation of additional foam. Surprisingly, and contrary to all expectation, that is not the case. Instead, the liquid jets generated by the foam breaker suffice to circulate and destroy the foam. Since, in so doing, it increases the interface between the liquid and gaseous phases, it also reduces the residence (life) time of the individual foam bubbles.

One of the structural advantages—in addition to the functional ones—of the foam breaker according to the invention, is its simplicity. When used in fermentation reactors having a rotor (shaped as a shaft or otherwise) the invention can be retrofitted to the existing equipment by simply mounting the rod 5 or the tubes 5a, 5b on the rotor. Moreover, aside from the bending required to impart the desired curvature, these tubes or this rod require no further processing or machining of any kind. Due to the constant spraying of liquid into and through the foam, and the resulting rapid destruction of the foam and its readmixing with the liquid phase, local separations do not occur. If the rotational speed of the rotor is increased—which leads inherently to an increase in the foam formation—the rate of foam destruction by the inventive foam breaker increases correspondingly, so that no control equipment is needed to adapt the operation of the breaker to that of the rotor.

It goes without saying that tubes of different inner diameter may be used, as may be desired to adapt the breaker to the respective reactor size and operating conditions. Also, the relationship between the inner diameter at the tube inlet and the inner diameter at the tube outlet (and even of the inner diameter in between the inlet and outlet) may be selected at will to accommodate the flow speed of the liquid through the tubes to the requirements and conditions of a particular fermentation process.

More than two tubes or rods may be used and these may be arranged at the same level of the reactor vessel but with their inlets and outlets at different distances from the rotor. It is also possible to use two or more rods or tubes as illustrated in the drawing and to install additional rods or tubes at higher and/or lower levels. Another possibility is to mount as many rod or tubes as desired at one level but with their inlets being located at different levels and their outlets also being located at different levels.

While the invention has been illustrated and described as embodied in a foam breaker for fermentation reactors, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims:

1. A mechanical foam breaker for destroying a foam layer formed atop a liquid phase in gas/liquid reactors having a rotor, comprising at least one curved tube having an inlet and an outlet; and means for mounting said tube on the rotor at an oblique angle to the axis of rotation so that a portion of the liquid phase in the reactor is scooped up by said inlet and forced through the tube during rotation of the rotor, to emerge from the outlet as a liquid jet which penetrates the foam layer.

2. A foam breaker as defined in claim 1; further comprising at least one additional curved tube similar to the first-mentioned tube, said means mounting said tubes radially symmetrical relative to the rotor.

3. A foam breaker as defined in claim 2, said tubes being so mounted that when the rotor is rotating said inlets are immersed in the liquid phase to an extent depending upon the angle included between the tubes and the axis of rotation of the rotor.

4. A foam breaker as defined in claim 2, said tubes being curved in the direction of rotation of the rotor.

5. A foam breaker as defined in claim 2, said means comprising a bar mountable on the rotor so as to extend transverse to the axis of rotation thereof, a pair of tube-holding brackets, and mounting screws for mounting each of said holding brackets at an end portion of the bar so as to hold a respective one of said tubes.

6. A foam breaker as defined in claim 5, said means further including stabilizing screws for said holding brackets.

7. A foam breaker as defined in claim 2, said tubes having inner diameters which are selectable at will.

8. A foam breaker as defined in claim 2, said tubes having at said inlets an inner diameter which is different from the inner diameter at said outlets.

9. A foam breaker as defined in claim 1; further comprising additional tubes similar to the first-mentioned tube, different ones of said tubes being mounted on said rotor at different axial spacing relative thereto.

10. A foam breaker as defined in claim 1; further comprising additional tubes similar to the first-mentioned tube, said tubes being mounted on said rotor at different vertical locations of the rotor.

11. A mechanical foam breaker for destroying a foam layer formed atop a liquid phase in gas/liquid reactors having a rotor, comprising at least one elongated curved generally rod-shaped element; and means for mounting said element on the rotor at an oblique angle to the axis of rotation so that said element alternately at least partially immerses in and emerges from the liquid phase in the reactor, thereby splashing a portion of the liquid phase into the foam layer.

12. A foam breaker as defined in claim 15, wherein said element is of solid cross-section.

13. In a gas/liquid reactor, a combination comprising a vessel for receiving a liquid phase and a gaseous phase; a rotor mounted in said vessel for rotation on an upright axis so as to agitate and mix together the liquid phase and the gaseous phase in the vessel, with the resultant formation of a foam layer above the upper level of the liquid phase; and foam-breaking means for destroying the foam layer, comprising at least two curved tubes each having an inlet and an outlet, and means for mounting said tubes on the rotor for movement therewith and at a level at which liquid of the liquid phase is scooped up by said inlets and forced through the tubes to emerge from the outlets as liquid jets which penetrate and destroy the foam of said layer.

* * * * *